(12) United States Patent
Marble et al.

(10) Patent No.: US 7,733,091 B2
(45) Date of Patent: Jun. 8, 2010

(54) PROBE, SYSTEM AND METHOD SUITABLE FOR UNILATERAL NUCLEAR MAGNETIC RESONANCE

(75) Inventors: Andrew E. Marble, Maberly (CA); Joshua J. Young, St. Andrews (CA); Igor V. Mastikhin, Hanwell (CA); Bruce G. Colpitts, Fredericton (CA); Bruce J. Balcom, Fredericton (CA)

(73) Assignee: University of New Brunswick, Fredericton, New Brunswick ( * ) Notice: Subject to any disclaimer, the term of this patent is extended or adjusted under 35 U.S.C. 154(b) by 0 days.

(21) Appl. No.: 11/898,132

(22) Filed: Sep. 10, 2007

(65) Prior Publication Data

US 2009/0066331 A1 Mar. 12, 2009

(51) Int. Cl.
*G01V 3/00* (2006.01)

(52) U.S. Cl. .......... 324/322; 324/318; 324/307; 324/321

(58) Field of Classification Search ......... 324/318–322; 600/407–435; 333/219–235
See application file for complete search history.

(56) References Cited

U.S. PATENT DOCUMENTS

| | | | |
|---|---|---|---|
| 5,390,673 A | 2/1995 | Kikinis | |
| 5,959,454 A * | 9/1999 | Westphal et al. | 324/320 |
| 6,489,767 B1 * | 12/2002 | Prado et al. | 324/318 |
| 6,489,872 B1 * | 12/2002 | Fukushima et al. | 335/299 |
| 6,657,433 B1 * | 12/2003 | Locatelli et al. | 324/318 |
| 6,828,892 B1 | 12/2004 | Fukushima et al. | |
| 7,075,298 B2 * | 7/2006 | Mityushin et al. | 324/303 |
| 7,132,829 B2 * | 11/2006 | Hudson et al. | 324/318 |
| 7,271,592 B1 * | 9/2007 | Gerald et al. | 324/321 |
| 7,319,326 B2 * | 1/2008 | Balcom et al. | 324/318 |
| 7,358,734 B2 * | 4/2008 | Blumich et al. | 324/318 |
| 7,486,078 B1 * | 2/2009 | Gerald et al. | 324/321 |
| 7,495,443 B2 * | 2/2009 | Leussler et al. | 324/318 |
| 2002/0101241 A1 * | 8/2002 | Chui | 324/319 |
| 2004/0052116 A1 * | 3/2004 | Mityushin et al. | 365/200 |
| 2006/0066310 A1 * | 3/2006 | Balcom et al. | 324/318 |
| 2007/0046408 A1 * | 3/2007 | Shim | 335/296 |
| 2007/0182413 A1 * | 8/2007 | Blumich et al. | 324/318 |
| 2008/0129292 A1 * | 6/2008 | Leussler et al. | 324/318 |
| 2009/0066331 A1 * | 3/2009 | Marble et al. | 324/318 |

OTHER PUBLICATIONS

F. Casanova, and B. Bllumich, Two-dimensional imaging with a single-sided NMR probe, J Magn. Reson. 163, 38-45 (2003).*

(Continued)

*Primary Examiner*—Brij B Shrivastav
*Assistant Examiner*—Tiffany A Fetzner
(74) *Attorney, Agent, or Firm*—Eugene F. Derényi; Stikeman Elliott LLP

(57) ABSTRACT

A probe suitable for use in unilateral nuclear magnetic resonance imaging and adapted to be embedded in a sample to be analysed, the probe comprising; a static magnetic field generator; a radiofrequency magnetic field generator adjacent to the static magnetic field generator; a circuit controlling the frequency response of the radiofrequency magnetic field generator, adjacent to the static magnetic field generator; an input cable coupled to the frequency control circuit and the frequency control circuit coupled to the radiofrequency magnetic field generator.

18 Claims, 11 Drawing Sheets

OTHER PUBLICATIONS

P.J. Prado, NMR hand-held moisture sensor, Magn. Reson. Imaging 19, 505-508 (2001).*

J. Perlo, F. Casanova, and B. Blumich, 3D imaging with a single-sided sensor: as open tomograph, J. Magn. Reson. 166, 228-235 (2004).*

P. J. Prado, Single sided imaging sensor, Magn. Reson. Imaging. 21,397-400 (2003).*

Blumich et al., The NMR Mouse, a Mobile Universal Surface Explorer, Journal of Magnetic resonance, 1996, Series A 122, pp. 104-109, Academic Press.

Boguszynzka, j. et al., Magnetic resonance studies of cement based materials in inhomogeneous magnetic fields, Cement and Concrete Research, 2005, 35, pp. 2033-2040.

Blumich et al., Simple NMR-Mouse with a Bar Magnet, Concepts in Magnetic Resonance, Dec. 2002, vol. 15(4), pp. 255-261, Wiley.

* cited by examiner

PROBE, SYSTEM AND METHOD SUITABLE FOR UNILATERAL NUCLEAR MAGNETIC RESONANCE

CROSS-REFERENCE TO RELATED APPLICATIONS

Not applicable.

MICROFICHE APPENDIX

Not applicable.

TECHNICAL FIELD

This application relates to nuclear magnetic resonance techniques in general, and to a probe, system and method suitable for unilateral nuclear magnetic resonance, in particular.

BACKGROUND OF THE INVENTION

Despite growing interest in magnetic resonance of porous materials such as soils and concrete, critical limitations exist in terms of the types of measurements that can be made. Both spectroscopic and spatially resolved studies requiring superconducting magnets can only be carried out on samples of limited size. New advances in open, portable NMR instrumentation allow bulk relaxation and diffusion measurements to be made on arbitrarily large samples such as described in G. Eidmann, R. Savelsberg, P. Blümler, B. Blümich, J. Magn. Res. A 1996; 122:104-109. However, experiments of this type are limited by the penetration depth of $B_0$ and $B_1$. This constraint has permitted higher field (10-20 MHz) near surface studies (see Boguszynska, J. et al., Cem. Concr. Res, 2005 35:2033-2040), along with lower field measurements at a greater, but still limited, depth.

In many situations, it may be desirable to measure NMR parameters from deep within a sample. Examples in the porous media regime could include larger concrete structures and soil formations. Previous work has used RF coils embedded within concrete samples in order to alleviate the $B_1$ penetration problem (see Boguszynska, above).

Extending this idea, a small, low cost NMR sensor suitable to be embedded within a large sample has been developed. NdFeB disk magnets provide a local $B_0$ field for a 1H resonant frequency of between 6-10 MHz depending on the design. A printed circuit board surface coil is located immediately above one face of the magnets, and tuned to resonance with capacitors on the opposite face. The entire arrangement is connected to a 2.5 mm diameter coaxial cable, and encased in epoxy. The inhomogeneous $B_0$ and $B_1$ fields define a local sensitive spot in which bulk relaxation time or diffusion measurements can be made.

According to one aspect of the present invention, there is provided a probe suitable for use in unilateral nuclear magnetic resonance imaging and adapted to be embedded in a sample to be analysed, the probe comprising; a magnet having a north and south pole; a radiofrequency coil adjacent one of the poles of the magnet; a capacitive tuning circuit adjacent the other pole of the magnet; a coaxial cable electrically connected to the tuning circuit and the tuning circuit electrically connected to the coil.

According to another aspect of the present invention, there is provided a probe suitable for use in unilateral nuclear magnetic resonance imaging and adapted to be embedded in a sample to be analysed, the probe comprising; a static magnetic field generator; a radiofrequency magnetic field generator adjacent to the static magnetic field generator; a circuit controlling the frequency response of the radiofrequency magnetic field generator, adjacent to the static magnetic field generator; an input cable coupled to the frequency control circuit and the frequency control circuit coupled to the radiofrequency magnetic field generator.

According to another aspect of the present invention, there is provided a method for magnetic resonance imaging of a sample comprising the step of embedding a probe in the sample to be imaged.

According to another aspect of the present invention, there is provided a system for use in unilateral nuclear magnetic resonance imaging comprising: a probe adapted to be embedded in a sample to be analysed, an RF supply module connected to probe suitable for generating an RF signal compatible with nuclear magnetic resonance.

An RF coil suitable for nuclear magnetic resonance imaging wherein the coil in bowtie shaped. The coil may have multiple windings.

Other aspects and features of the present invention will become apparent to those ordinarily skilled in the art upon review of the following description of specific embodiments of a probe, system and method suitable for unilateral nuclear magnetic resonance in conjunction with the accompanying drawing figures.

BRIEF DESCRIPTION OF THE DRAWINGS

Embodiments of the present invention will now be described, by way of example only, with reference to the accompanying drawing figures, wherein.

Like reference numerals are used in different figures to denote similar elements.

DETAILED DESCRIPTION OF THE DRAWINGS

Figure 1:
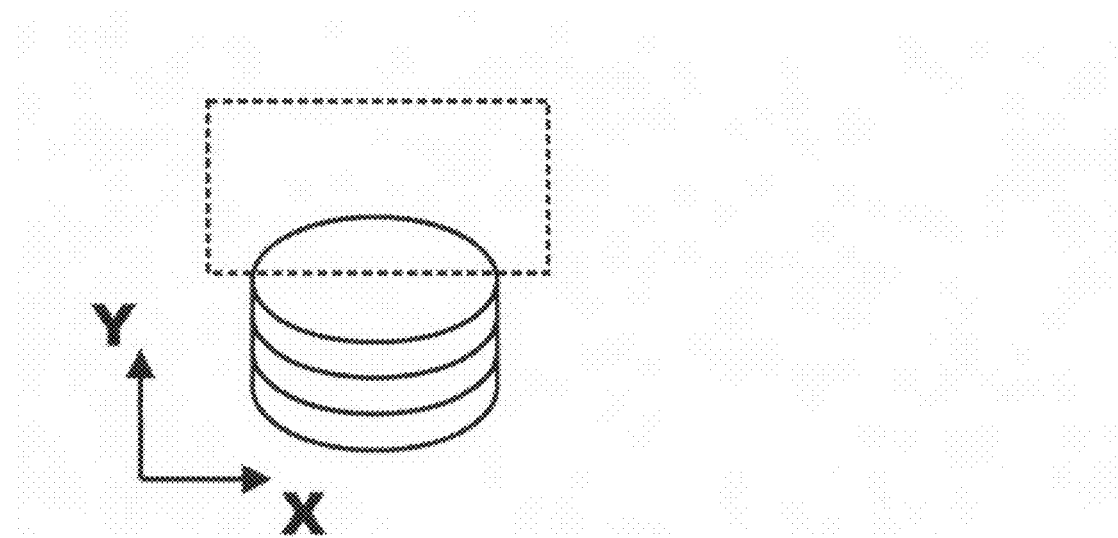
FIG. 1 is a schematic diagram of an array of three disc magnets and an associated magnetic field of interest.
Figure 2:
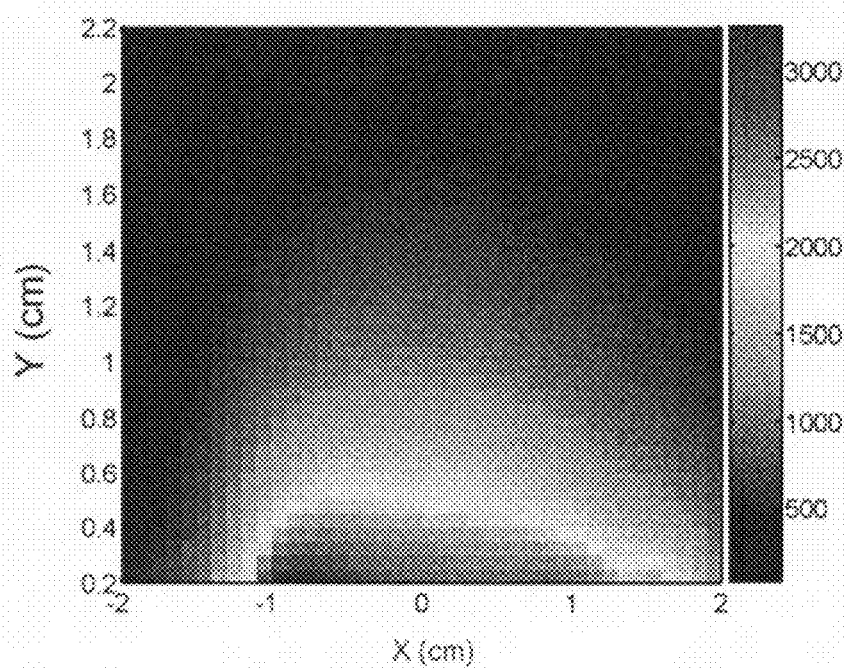
FIG. 2 is an image of the magnetic scalar potential for the array of magnets of FIG. 1.

Referring to FIGS. 1 and 2, the measured magnetic field magnitude over a stack (array) of three disk magnets is shown. About 3 mm above the magnets, the field is ~2500 G (~10.5 MHz$^1$H). The field is inhomogeneous, due to the single sided nature of the device as well as inhomogeneous magnetization in the low quality magnets.

Figure 3:
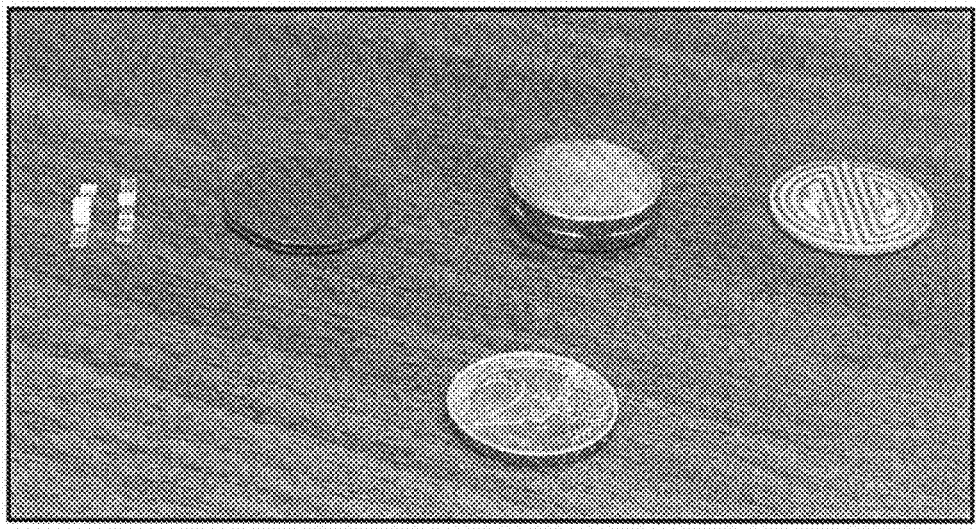
FIG. 3 is a photograph of components of a probe according to the present invention.

Referring to FIG. 3, components of the probe (also commonly referred to as a sensor) are shown. From left to right the components of the top row are: two capacitors; two discs made of iron which serve as a yoke in the assembled sensor; two disc magnets made of NdFeB; and a radiofrequency (RF) coil milled on a printed circuit board. The RF coil is a modified "double-d" design. The printed circuit board in the assembled sensor sits on top of the magnets to generate a field centred above the top of the magnet stack. The two Euro coin shown blow the row of components is to show scale and does not form part of the invention. The iron yoke which in the assembled sensor sits below the magnets, can be used to adjust the field strength above the magnets. The RF coil is tuned to a frequency suitable for nuclear magnetic resonance in a volume above the coil frequency with small, fixed value capacitors mounted to a PC board below the magnets, and fed through a thin coaxial cable. In some embodiments, the discs of magnets may be replaced by one magnet of a size comparable to the combined size of the two disc magnets. In some embodiments, more than two disc magnets may be used.

Figure 4:
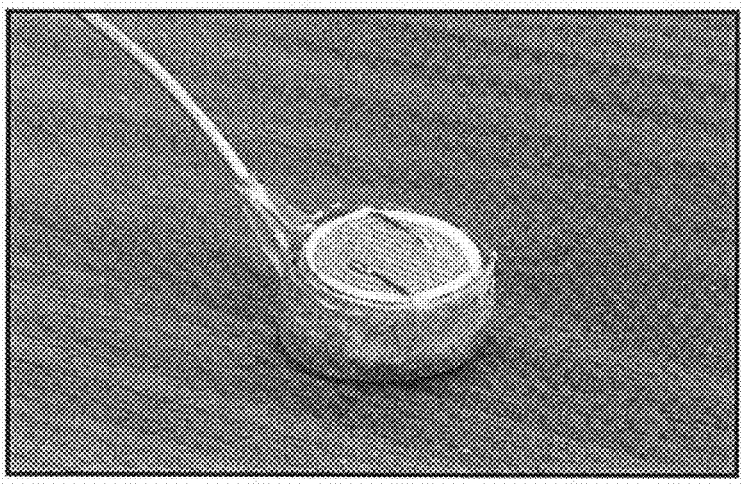
FIG. 4 is photograph of an assembled probe according to the present invention.

Referring to FIG. 4, an assembled sensor according to the present invention is shown. The sensor includes the components shown in FIG. 3. The sensor is small relative to the dimensions of the sample in which it is to be embedded (wet cement in this example) and is approximately 3 mm in diameter and 2 cm in thickness and includes the components shown in FIG. 2. The sensor of FIG. 4 is encased in a water proof epoxy to protect the components in the wet cement environment. The nominal static field value above the sensor gives a Larmor frequency of 8.08 MHz$^1$H.

Figure 5:
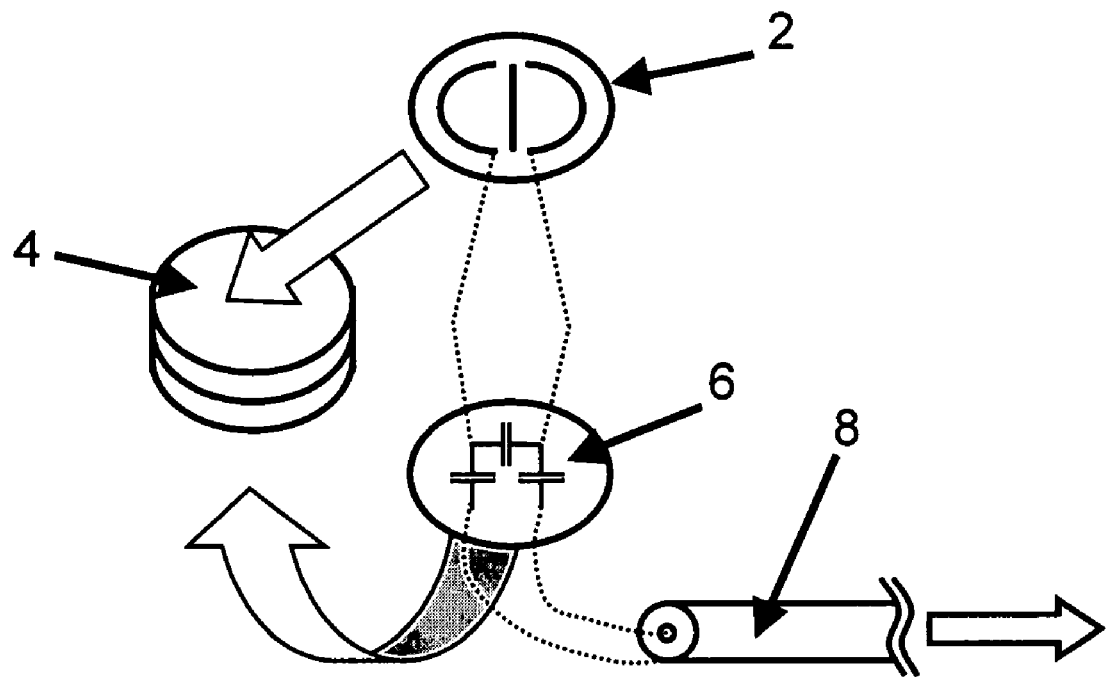
FIG. 5 is a schematic diagram showing the interconnection of components of the probe of FIG. 4.

Referring to FIG. 5, the radiofrequency coil 2 is fixed atop the magnets 4. The coil is connected by wire leads (shown in dashed lines) to a capacitive tuning circuit 6 mounted on a circuit board and fixed to the bottom of the magnets. The tuned circuit is connected to a coaxial cable 8, which is attached to the RF supply module and signal detection module as described with reference to FIG. 11.

Measurements were made using the sensor of FIG. 4, both of moisture content in sand, and signal amplitude/relaxation times in curing concrete. In each case, a sensor was immersed in sand/concrete and a Bruker Minispec spectrometer was used for RF supply, NMR signal detection and experimental control. These measurements are shown here as a proof of principle. In the case of the moisture content measurements, the signal intensity correlates well with the measured moisture content. For the curing concrete, further study is required to correlate measurements with relevant material parameters.

Figure 6:
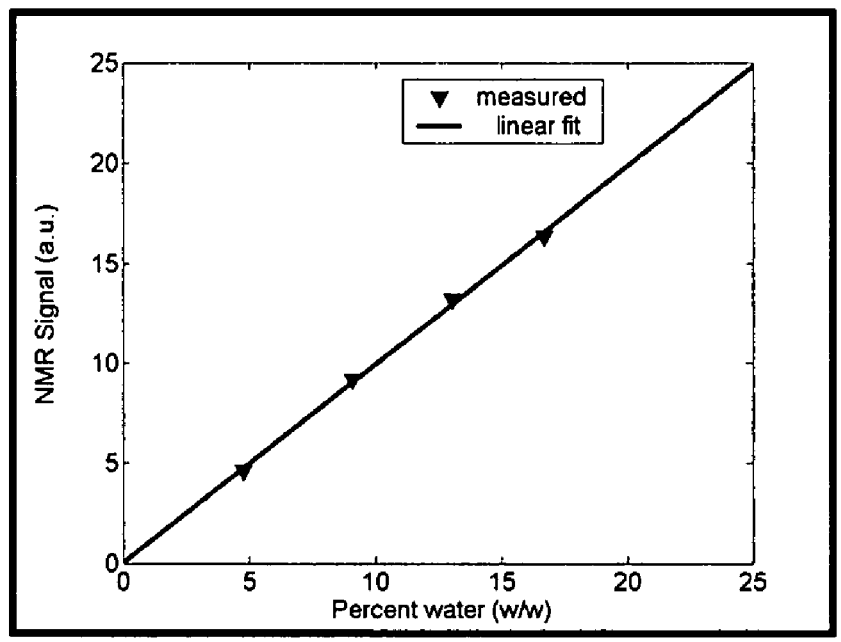
FIG. 6 is a plot of NMR measurements of the moisture content of a sand sample acquired according to the invention.

Referring to FIG. 6, NMR measurements of the moisture content of sand. The sensor was immersed in wet sands with different weight percentages of water. A CPMG sequence was used to measure the moisture content, with 32 echoes, an echo time of 0.2 ms, and 512 scans for an acquisition time of 9 minutes per point. The echoes were co-added to obtain the signal. A linear relationship between the water content and MR signal intensity is observed.

Figure 7:
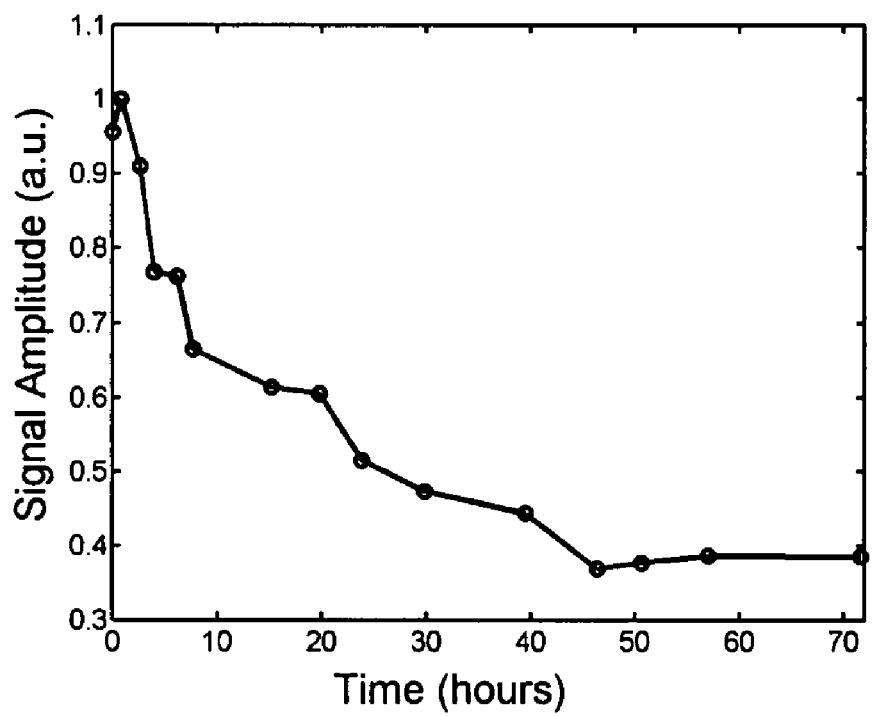
FIG. 7 is a plot of signal amplitude as a function of time measured with an apparatus according to the invention embedded in curing cement.

Referring to FIG. 7, Signal amplitude as a function of time measured with a sensor embedded in curing ASTM Type 1 cement, w/c ratio 0.45. The first two echoes in a CPMG sequence (TE=0.168 ms, 8192 scans) were averaged to give the signal.

Figure 8:
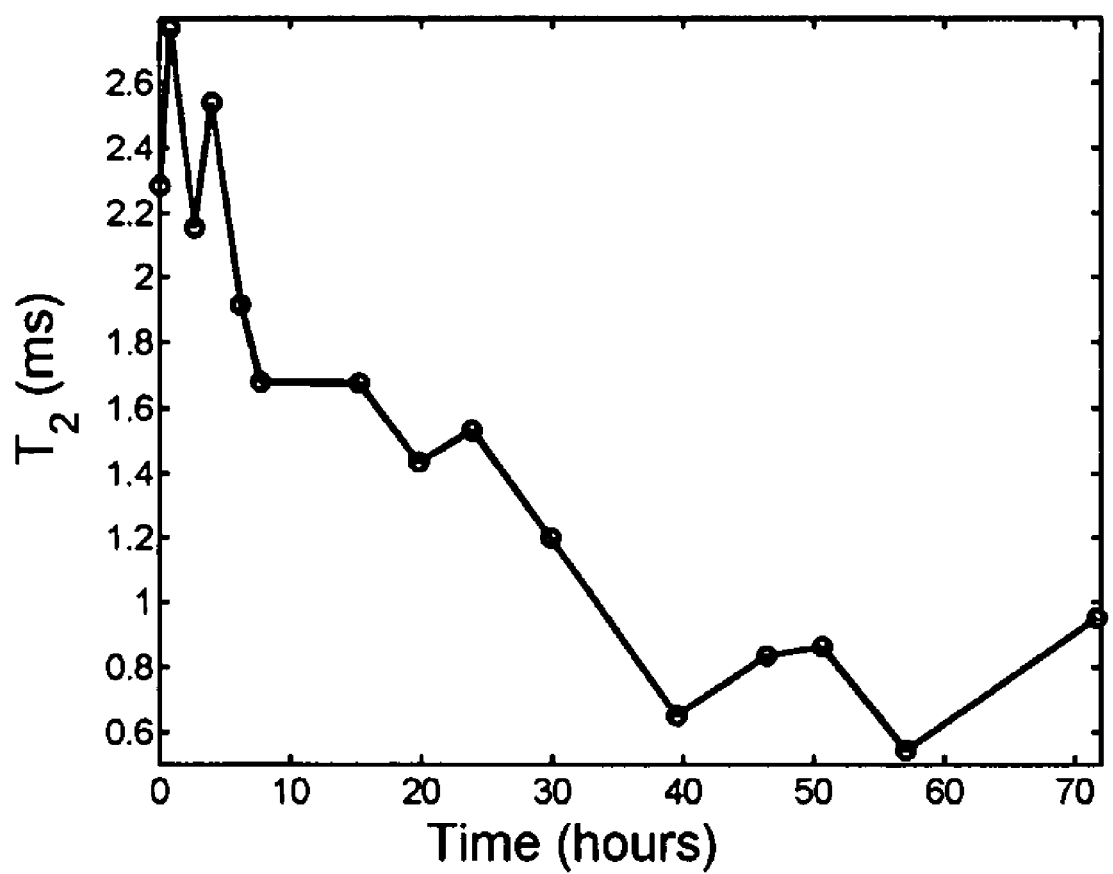
FIG. 8 is a plot of apparent T2 measured by Carr-Purcell-Meiboom-Gill (CPMG) method in a curing ASTM Type 1 cement sample.

Referring to FIG. 8, apparent T2 measured by CPMG (TE=0.168 ms, 8192 scans) in a curing ASTM Type 1 cement sample. Because of the grossly inhomogeneous field, the relaxation constant is a combination of T2 and diffusive attenuation.

Figure 9:
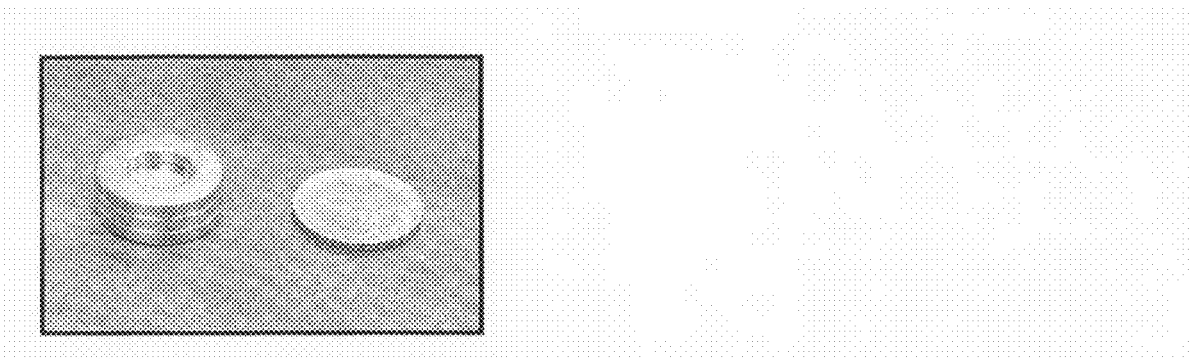
FIG. 9 is another embodiment of an apparatus according to the present invention.
Figure 10:
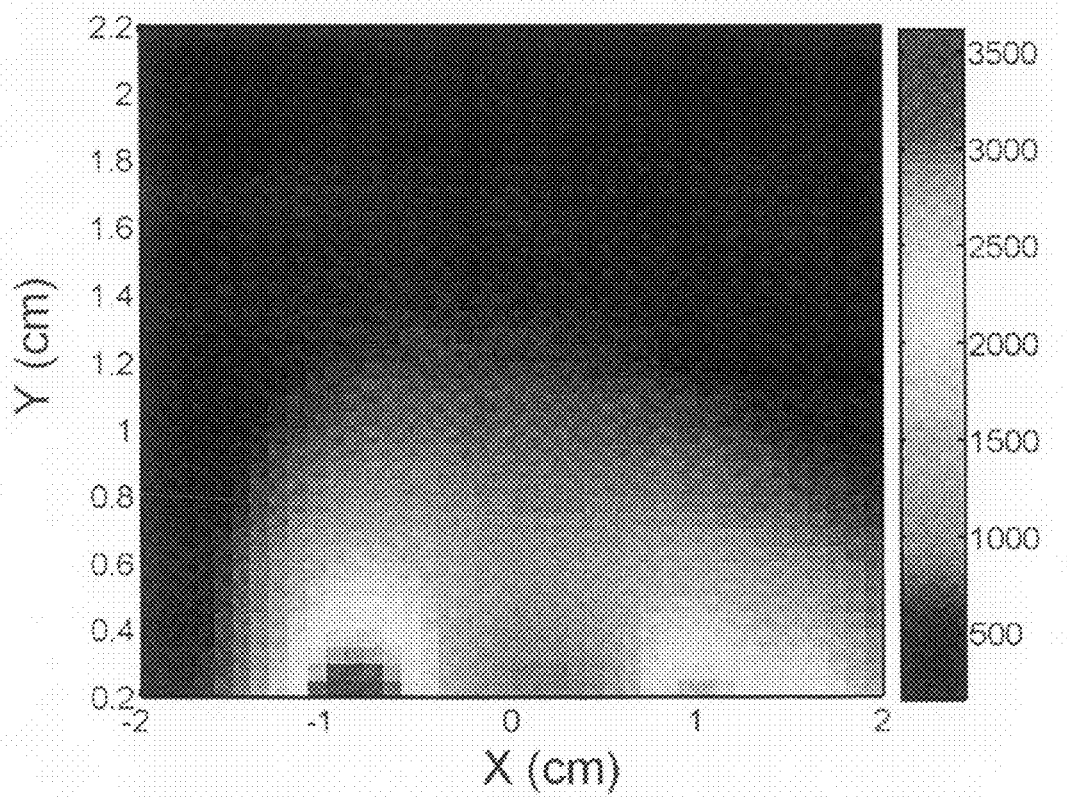
FIG. 10 is an image of the magnetic scalar potential for the sensor of FIG. 9.

Referring to FIG. 9, an alternate magnet arrangement producing a more homogeneous field a more homogeneous field than the embodiment of FIG. 1, at a frequency around 6 MHz. A washer magnet is placed on top of a stack of disk magnets, giving a saddle point in the field. While the field is slightly lower in this arrangement, the saddle point ensures that signal can be obtained from a larger volume, increasing sensitivity. Furthermore, the gradient around the saddle point is low, mitigating diffusive attenuation.

Figure 15:
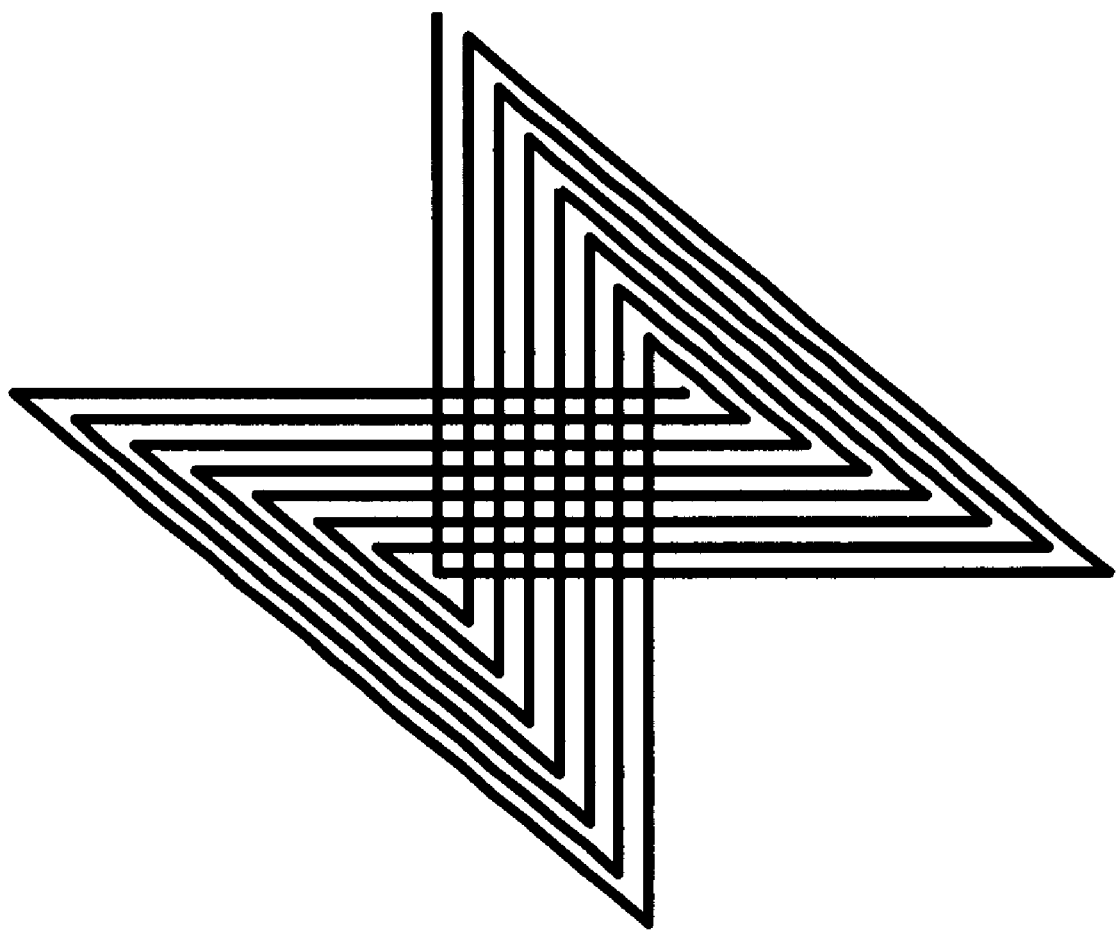
FIG. 15 is a "bowtie" coil comprised of multiple coils.

Alternatively, it will be understood by those skilled in the art that other magnet designs may be employed depending upon the magnetic field desired. For example, a magnet with two north poles and two south poles of the type in illustrated in FIG. 15 could be used as part of a probe according to the invention.

Figure 11:
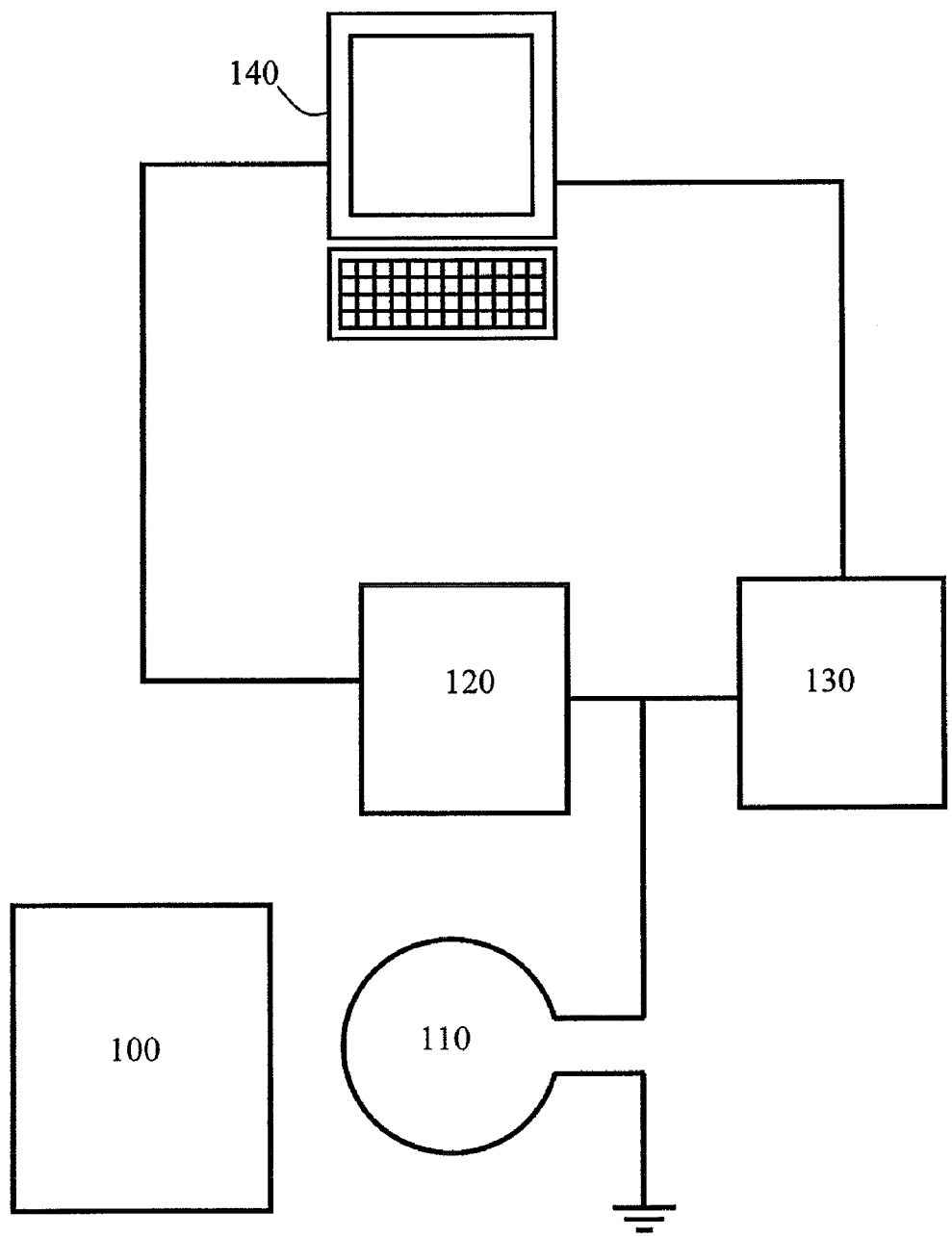
FIG. 11 is a block diagram of an embodiment of and NMR apparatus provided in accordance with the present invention.

FIG. 11 is a block diagram of one embodiment of an NMR system provided in accordance with the present invention. The magnetic 100 produces a suitable static magnetic field in a region of interest. The dynamic field generator 110 generates a dynamic radiofrequency magnetic field in the region of interest. The RF supply module 120 is connected to the dynamic field generator and supplies an RF signal compatible with nuclear magnetic resonance to the dynamic field generator. The detection module 130 detects nuclear magnetic resonance signals induced in the dynamic field generator. The RF supply module is controlled with a computer 140, and the signals detected by the detection module are recorded and processed on the computer.

Alternate patterns may be used for the printed circuit board for the probes according to the present invention and may have application for other NMR probes. Single-sided magnetic resonance measurements require single-sided or surface coils for $B_1$ generation and signal detection. The fundamental constraint in coil design is that $B_1$ must be orthogonal to $B_0$. For the case where $B_1$ must be normal to the magnet surface, a circular surface coil is the clear choice.

In many cases, it is desirable to have $B_0$ normal to the magnet surface, and $B_1$ must therefore be generated parallel to the surface of the coil in order to meet the orthogonality condition necessary for magnetic resonance. This can be achieved in practice by a sheet of RF current, approximated by several parallel wires. However, in this arrangement, additional wire is necessary to form a closed loop of current. Along with increasing the resistance of the coil, this additional wire generates a spurious $B_1$ field. This field can be parallel to $B_0$, and therefore not useable for NMR purposes, or outside the desired sensitive volume of the coil. In the first case, the field effectively reduces the filling factor and directly increases the measurement noise. In the second case, signal from unwanted regions of a sample may be measured, affecting experimental results.

In selecting a coil design for generating a field parallel to the surface of the coil, the goal is to generate the strongest possible field in a region of interest (ROI), while reducing spurious fields as much as possible.

Figure 12:
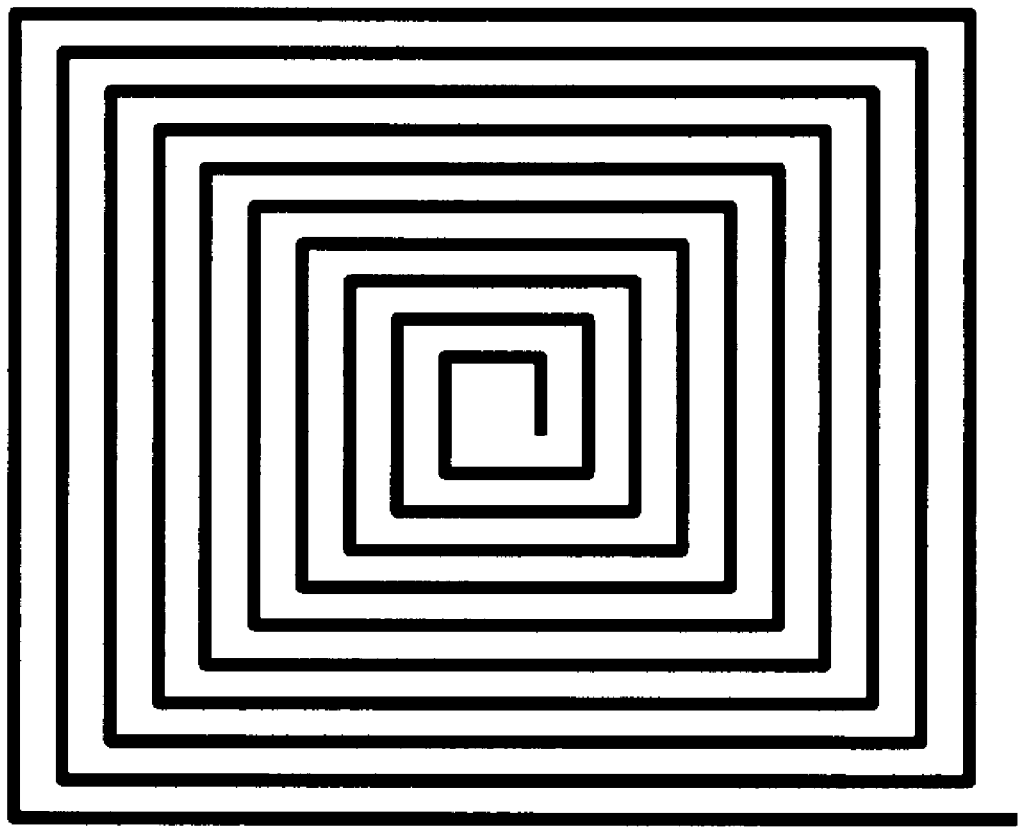
FIG. 12 is a spiral coil.
Figure 13:
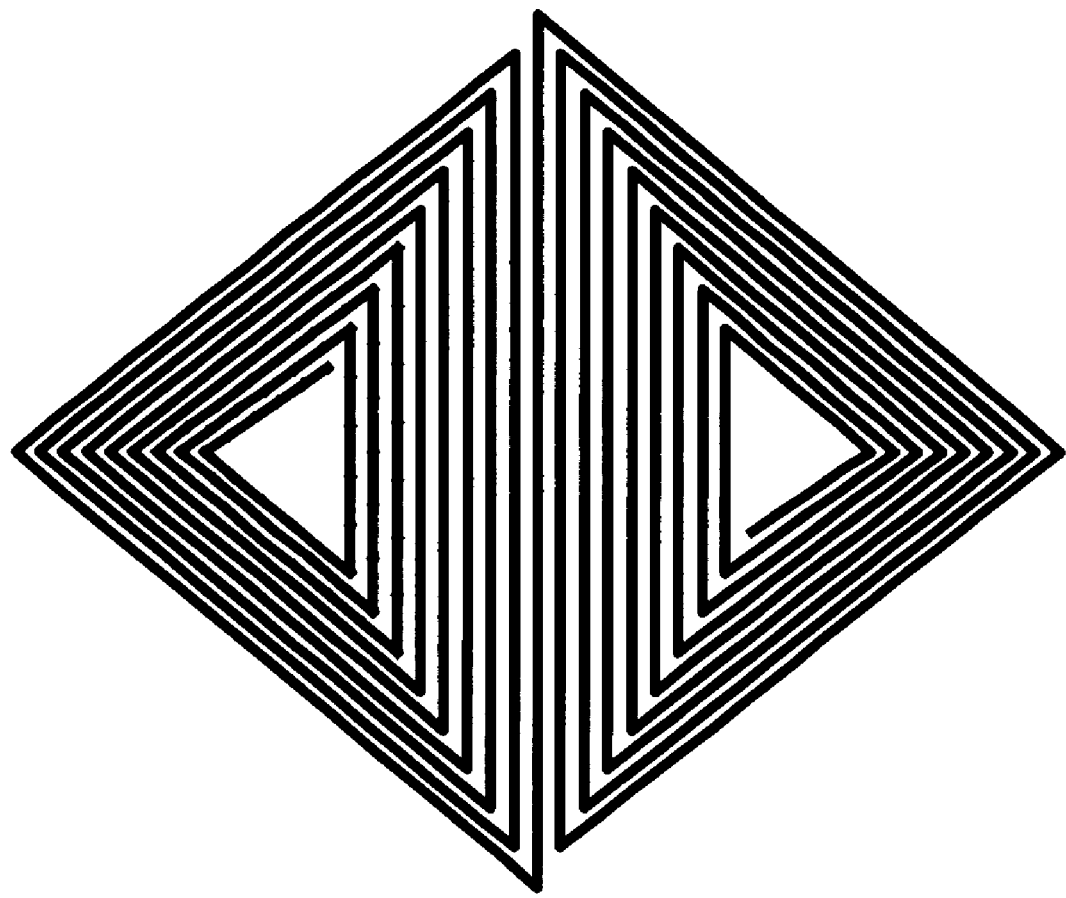
FIG. 13 is a modified DD coil.
Figure 14:
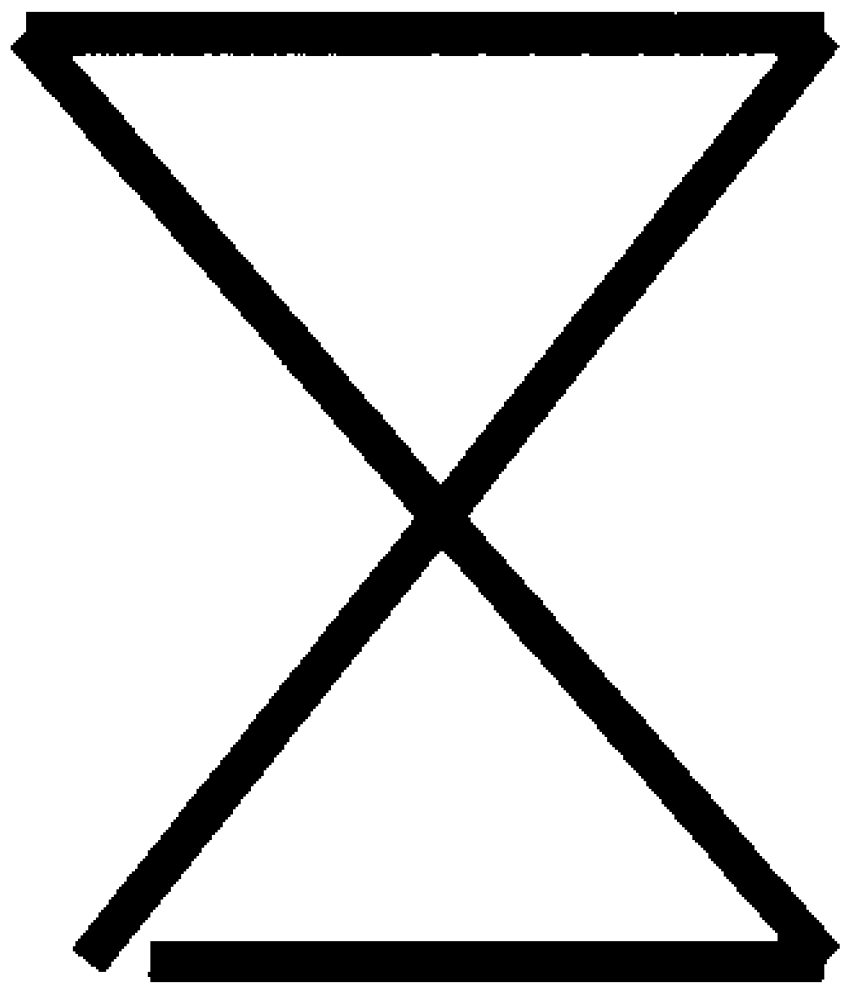
FIG. 14 is a "bowtie" coil comprised of a single coil.

FIG. 12 depicts a "spiral" coil, FIG. 13 a "modified DD' coil and FIG. 14, a "bowtie" coil.

Coils using the spiral, modified DD and bowtie patterns were manufactured from wire epoxied to a thin substrate. The coil patterns were first simulated using the Biot-Savart law, and the transverse field intensity integrated over a 1 cm depth to give the plots shown. A 5 cm by 5 cm by 1 cm thick rubber sample was then imaged at 8.3 MHz using the SPRITE MRI technique using each coil.

The spiral coil gives a relatively uniform field over a ring shaped region, and results in the highest signal intensity when tested. No signal, however, is derived from the centre of the sample. In many unilateral applications, it is this region that is most important in terms of $B_0$ characteristics, and the spiral coil may not be an appropriate choice.

The double-d coil features comparable signal intensity to that of the spiral coil, but the image indicates that more of this signal originates from the center of the coil. There is a large amount of signal from the coil return paths, with an intensity of approximately half that of the center region.

The bowtie coil has a lower total signal, however the 2D image indicates that this coil has superior spatial selectivity, and a higher sensitivity in the central region than either the spiral or double-d coils. It will be understood that the number of windings can be varied according to the desired magnetic field profile and/or coil performance.

The above-described embodiments of the present invention are intended to be examples only. Those of skill in the art may effect alterations, modifications and variations to the particular embodiments without departing from the scope of the invention, which is set forth in the claims.

We claim:

1. A unilateral nuclear magnetic resonance imaging probe adapted to be embedded in a material sample to be analyzed wherein the probe is enclosed firmly in the sample, the probe comprising:
   a permanent magnet;
   a radiofrequency coil adjacent to a pole of the permanent magnet;
   a frequency control circuit that controls the frequency response of the radiofrequency coil the frequency control circuit being adjacent to the permanent magnet and also coupled to the radiofrequency coil; and
   an input cable coupled to the frequency control circuit.

2. The probe of claim 1, wherein the radiofrequency coil has at least one winding.

3. The probe of claim 1, wherein the radiofrequency coil is adjacent a pole of the permanent magnet and where the pole is not adjacent a pole of another permanent magnet.

4. The probe of claim 3, wherein the permanent magnet comprises at least two permanent magnets where the poles of all of the magnets are collinear on an axis passing through all of the magnets.

5. The probe of claim 4, wherein one of the magnets is washer-shaped.

6. The probe of claim 2, wherein the radiofrequency coil comprises a bowtie-shaped coil.

7. The probe of claim 2, wherein the radiofrequency coil comprises a double-d shaped coil.

8. The probe according to claim 1, wherein the sample comprises a non-human sample.

9. The probe according to claim 8, wherein the sample is selected from the group consisting of cement, concrete, a structure and soil.

10. A method for in-situ measurement nuclear magnetic resonance parameters of a sample comprising the steps of:
    embedding the probe of claim 1 in the sample wherein the probe is enclosed firmly in the sample;
    connecting the probe to a spectrometer suitable for nuclear magnetic resonance measurement;
    generating $B_0$ and $B_1$ fields in order to define a local sensitive spot;
    taking, NMR measurements in the sensitive spot, selected from the group comprising bulk relaxation time and diffusion measurements.

11. The method of claim 10, wherein the sample is selected from the group consisting of cement, concrete, a structure and soil.

12. The method of claim 10, wherein in the step of embedding the probe, the probe is permanently or semi-permanently embedded in the sample.

13. A unilateral nuclear magnetic resonance imaging system comprising:
    a probe adapted to be embedded in a non-human sample to be analyzed wherein the probe is enclosed firmly in the sample,
    the probe comprising:
        a permanent magnet;
        a radiofrequency coil;
        a radiofrequency supply module connected to the radiofrequency coil, capable of generating a radiofrequency signal compatible with nuclear magnetic resonance.

14. The system of claim 13, further comprising a computer that controls the radiofrequency supply module and the recording and processing signals detected by the module.

15. The sample of claim 13, wherein the sample is selected from the group consisting of cement, concrete, a structure and soil.

16. The system of claim 14, wherein the radiofrequency coil has multiple windings.

17. The system of claim 16, wherein the coil is bowtie shaped.

18. The system of claim 16, wherein the radiofrequency coil is double-d shaped.

* * * * *